US012655080B2

(12) United States Patent
Tjärnehov

(10) Patent No.: US 12,655,080 B2
(45) Date of Patent: Jun. 16, 2026

(54) PROCESS AND REACTION SYSTEM FOR THE PREPARATION OF METHANOL

(71) Applicant: Topsoe A/S, Kgs. Lyngby (DK)

(72) Inventor: Emil Andreas Tjärnehov, Limhamn (SE)

(73) Assignee: Topsoe A/S, Kgs. Lyngby (DK)

( * ) Notice: Subject to any disclaimer, the term of this patent is extended or adjusted under 35 U.S.C. 154(b) by 896 days.

(21) Appl. No.: 17/796,197

(22) PCT Filed: Feb. 1, 2021

(86) PCT No.: PCT/EP2021/052262
§ 371 (c)(1),
(2) Date: Jul. 28, 2022

(87) PCT Pub. No.: WO2021/156179
PCT Pub. Date: Aug. 12, 2021

(65) Prior Publication Data
US 2023/0058914 A1 Feb. 23, 2023

(30) Foreign Application Priority Data
Feb. 5, 2020 (DK) ............................ PA 2020 00146

(51) Int. Cl.
*C07C 29/152* (2006.01)
*B01J 19/24* (2006.01)
*C07C 29/78* (2006.01)

(52) U.S. Cl.
CPC ........... *C07C 29/152* (2013.01); *B01J 19/245* (2013.01); *C07C 29/78* (2013.01)

(58) Field of Classification Search
CPC ....... B01J 8/00; B01J 8/001; B01J 8/02; B01J 8/04; B01J 8/0496; B01J 19/00; B01J 19/24; B01J 19/245; B01J 2208/00; B01J 2208/00008; B01J 2208/00017; B01J 2208/0053; C07C 29/00; C07C 29/15; C07C 29/151; C07C 29/152; C07C 29/74–78; C07C 31/00; C07C 31/02; C07C 31/04
See application file for complete search history.

(56) References Cited

U.S. PATENT DOCUMENTS

| | | | | |
|---|---|---|---|---|
| 9,505,689 | B2 * | 11/2016 | Almqvist | ............. B01J 19/2445 |
| 10,308,575 | B2 | 6/2019 | Yiu | |
| 2015/0175509 | A1 * | 6/2015 | Almqvist | ............. C07C 29/152 |
| | | | | 518/705 |
| 2017/0240492 | A1 * | 8/2017 | Kambe | .................... B01J 37/03 |
| 2019/0047931 | A1 | 2/2019 | Balthasar et al. | |
| 2019/0144359 | A1 | 5/2019 | Rajagopalan et al. | |

FOREIGN PATENT DOCUMENTS

| | | |
|---|---|---|
| CN | 104470630 A | 3/2015 |
| CN | 108463449 A | 8/2018 |
| GB | 2560784 A | 9/2018 |
| WO | WO 96/21634 A1 | 7/1996 |
| WO | WO 2009/007032 A1 | 1/2009 |
| WO | WO 2014/012601 A1 | 1/2014 |
| WO | WO 2016/149507 A1 | 9/2016 |
| WO | WO 2017/121980 A1 | 7/2017 |

OTHER PUBLICATIONS

SU 829609 A1 with machine translation (Year: 1981).*
J. Li et al., "Steady-State Process Simulation Study on Methanol Synthesis", Acta Petrolei Sinica, vol. 32, No. 3, pp. 539-545, Jun. 30, 2016.
Office Action and Search Report issued in corresponding Chinese Patent Application No. 202180012375.8, dated .Apr. 27, 2025.

* cited by examiner

*Primary Examiner* — Natasha E Young
(74) *Attorney, Agent, or Firm* — Blank Rome LLP

(57) ABSTRACT

A process and reaction system for preparation of methanol. A fresh methanol synthesis gas stream is introduced in a first methanol reaction unit in the presence of a methanol catalyst, resulting in a first effluent stream containing methanol and unconverted synthesis gas. A recycle gas stream containing the unconverted methanol synthesis gas contained in the first effluent stream and unconverted methanol synthesis gas from a second methanol reaction unit is introduced and reacted in the second methanol reaction unit in the presence of a methanol catalyst. The first effluent stream and a part of a second effluent stream containing methanol and the unconverted methanol synthesis gas from the second methanol reaction unit are combined, cooled, and separated into a methanol-containing liquid stream and the recycle stream. The remaining part of the second effluent stream is withdrawn as a purge gas stream prior to combining the first and second effluent streams.

6 Claims, No Drawings

PROCESS AND REACTION SYSTEM FOR THE PREPARATION OF METHANOL

This application is a U.S. National Stage Entry of International Patent Application Serial Number PCT/EP2021/052262, now WO 2021/156179, filed Feb. 1, 2021, which claims priority to Danish Patent Application No. DKPA 2020 00146, filed Feb. 5, 2020, the entire contents of all of which are incorporated herein by reference.

The present invention relates to a process for the preparation of methanol by catalytic conversion of methanol synthesis gas and a reaction system for carrying out the process.

More particularly, methanol is by the invention prepared in two reaction units, in which a first unit is operated in once-through mode on fresh synthesis gas optionally admixed with unconverted synthesis gas separated from effluent of a second reaction unit and in which the second reaction unit is operated in a synthesis loop with unconverted synthesis gas optionally admixed with fresh synthesis gas.

The reaction of carbon oxides and hydrogen to methanol is equilibrium limited and conversion of the synthesis gas to methanol per pass through a methanol catalyst is relatively low, even when using a high reactive synthesis gas.

Because of the low methanol production yield in a once-through methanol conversion process, the general practice in the art is to recycle unconverted synthesis gas separated from the reaction effluent and dilute the fresh synthesis gas with the recycle gas.

This typically results in the so-called methanol synthesis loop with one or more reactors connected in series being operated on fresh synthesis gas diluted with either recycled unconverted gas separated in a separator from the reactor effluents or on the reactor effluent containing methanol and unconverted synthesis gas. The recycle ratio (recycle gas: fresh synthesis feed gas) is 1:1 up to 7:1 in normal practice.

In methanol process designs with a once-through reaction unit and a reaction unit operated on recycled unconverted synthesis in a methanol synthesis loop, optimal gas compositions can be set to the once-through reaction unit or reaction unit operated on recycled unconverted synthesis by the recycle gas and feed bypass gas. The effluent from the once-through reaction unit is mixed with the effluent from the reaction unit in the synthesis loop. Produced methanol is separated from the mixed effluent after cooling upstream separation unit. Separated unconverted synthesis gas contained in the mixed effluent combined from the reaction units is recycled to the reaction unit in the synthesis loop.

In order to save equipment, the cooling and separation of the methanol containing effluent gas can be made in a combined cooling train. However, the combined cooling train will have mixed the two different recycle gasses, i.e one from the once through reaction unit and one from the synthesis loop reaction unit. To prevent built up of inert gases, a part of the combined recycled unconverted synthesis gas must be purged from the loop, thereby purging out more active reactants than necessary.

For the sake of simplicity, in the following description and claims the "once through reaction unit" is termed "first methanol methanol reaction unit" and the "synthesis loop reaction unit" is termed "second methanol reaction unit"

The term "methanol catalyst" used in the following description and in the claims refers to any catalyst being active in the conversion of hydrogen, carbon monoxide and carbon dioxide to methanol. Those catalysts are not part of the invention and are extensively disclosed in the patent literature.

Appropriate methanol catalysts for use in the invention are as an example the known copper-zinc based catalysts. The main principle of the invention is, thus, to withdraw a hot purge gas from the effluent of the second methanol reaction unit, prior to the effluent is combined with the effluent from the first reaction unit.

The hot purge gas will allow combined equipment in cooling train and at the highest content of inert components and the lowest activity, which allows more effective purging without losing too much reactants with only one extra small cooler.

The term "inerts" refers to components contained in methanol synthesis gas, which are not chemically reactive in the methanol synthesis.

Accordingly, this invention is a process for the preparation of methanol, comprising the steps of (a) providing a fresh methanol synthesis gas containing hydrogen, carbon monoxide and carbon dioxide;

(b)) introducing and reacting the fresh methanol synthesis gas stream in a first methanol reaction unit in presence of a methanol catalyst and obtaining a first effluent stream containing methanol and unconverted synthesis gas;

(c) providing a recycle gas stream containing the unconverted methanol synthesis gas contained in the first effluent stream and unconverted methanol synthesis gas from a second methanol reaction unit;

(d) introducing and reacting the recycle gas stream in the second methanol reaction unit in presence of a methanol catalyst;

(e) withdrawing a second effluent stream containing methanol and the unconverted methanol synthesis gas from the second methanol reaction unit;

(f)) combining the first and a part of the second effluent stream;

(g) cooling and separating the combined effluent into a methanol-containing liquid stream and the recycle stream; and (h) withdrawing the remaining part of the second effluent stream as a purge gas stream, wherein the remaining part of the second effluent stream is withdrawn as a purge gas stream prior to combining the first and second effluent stream.

In some applications of the process according to the invention, it will be desirous to adjust the module $M=(H_2-CO_2)/(CO+CO_2)$ of the fresh synthesis gas by addition of hydrogen to the gas. Hydrogen can be recovered from the purge gas and recycled to the process upstream the synthesis gas compressor.

Thus, in an embodiment of the invention at least a part of hydrogen contained in the purge gas stream is recovered and recycled to step b).

To provide optimum conditions for the methanol reaction in the first methanol reaction unit, a part of the recycle stream is introduced into the first methanol reaction unit in further an embodiment.

In still an embodiment, a part of the fresh methanol synthesis gas is introduced into the second methanol reaction unit to provide optimum condition for the methanol synthesis in the second methanol reaction unit.

The first and second methanol reaction unit can comprise one or more reactors selected from boiling water cooled reactors, gas cooled reactors, quench reactors and adiabatic operated reactors, connected in series and/or in parallel.

The invention provides furthermore reaction system for use in a process for the preparation of methanol, the system comprises a first and second methanol reaction unit containing each a methanol catalyst;

a process gas stream passageway for introducing a process gas stream of a fresh synthesis gas into the first methanol reaction unit and a circulation passageway for circulating unconverted synthesis gas to the second methanol reaction unit;

a first effluent passageway for withdrawing and passing a first methanol containing effluent stream from the first reaction unit to a mixing point in a second effluent passageway for withdrawing a second methanol containing effluent from the second reaction unit;

separating means arranged downstream the mixing point in the second effluent passageway for separating methanol from the unconverted synthesis gas;

a circulator arranged in the circulation passageway between the separating means arranged upstream the second methanol reaction unit; and a purge gas line connected to the circulation passageway and arranged upstream the mixing point in the second effluent passageway.

In an embodiment of the reaction system according to the invention, the purge gas line is connected to hydrogen recovery unit.

In an embodiment of the invention, a passageway is connected to the hydrogen recovery unit and to the process gas stream passageway for passing hydrogen to the gas stream of a fresh synthesis gas.

In an embodiment of the invention, the reaction system further comprises a passageway connected to the hydrogen recovery unit and to the process gas stream passageway for passing hydrogen to the gas stream of a fresh synthesis gas.

In an embodiment of the invention, the reaction system further comprises a split stream passageway for passing a part of the unconverted synthesis gas from the circulation passageway to the process gas stream passageway.

In an embodiment of the invention, the reaction system further comprises a split stream passageway for passing a part of the process gas stream of a fresh synthesis gas to the circulation passageway.

The first and second reaction unit in the above embodiments can comprise one or more methanol reactors selected from boiling water cooled reactors, gas cooled reactors, quench reactors and adiabatic operated reactors connected in series and/or in parallel.

The invention claimed is:

1. A reaction system for use in a process for the preparation of methanol, the system comprises a first methanol reaction unit and a second methanol reaction unit, each containing a methanol catalyst;

a process gas stream passageway for introducing a process gas stream of a fresh synthesis gas into the first methanol reaction unit and a circulation passageway for circulating unconverted synthesis gas to the second methanol reaction unit;

a first effluent passageway for withdrawing and passing a first methanol containing effluent stream from the first reaction unit to a mixing point in a second effluent passageway for withdrawing a second methanol containing effluent from the second reaction unit;

a separating means arranged downstream the mixing point in the second effluent passageway for separating methanol from the unconverted synthesis gas; and a circulator arranged in the circulation passageway between the separating means arranged upstream the second methanol reaction unit; and a purge gas line connected to the circulation passageway and arranged upstream the mixing point in the second effluent passageway.

2. The reaction system of claim 1, wherein the purge gas line is connected to a hydrogen recovery unit.

3. The reaction system of claim 2, further comprising a passageway connected to the hydrogen recovery unit and to the process gas stream passageway for passing hydrogen to the gas stream of a fresh synthesis gas.

4. The reaction system of claim 1, further comprising a split stream passageway for passing a part of the unconverted synthesis gas from the circulation passageway to the process gas stream passageway.

5. The reaction system of claim 1, further comprising a split stream passageway for passing a part of the process gas stream of a fresh synthesis gas to the circulation passageway.

6. The reaction system of claim 1, wherein the first and second reaction units comprise one or more methanol reactors selected from boiling water cooled reactors, gas cooled reactors, quench reactors and adiabatic operated reactors connected in series and/or in parallel.

* * * * *